US006471730B1

United States Patent
Lang et al.

(10) Patent No.: US 6,471,730 B1
(45) Date of Patent: Oct. 29, 2002

(54) DYEING COMPOSITION CONTAINING A LACCASE AND KERATINOUS FIBER DYEING METHODS USING SAME

(75) Inventors: Gérard Lang, Saint Prix (FR); Jean Cotteret, Verneuil/Seine (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/600,135

(22) Filed: Sep. 11, 2000

(51) Int. Cl.[7] .......................... A61K 7/13; C09B 67/100
(52) U.S. Cl. .................. 8/405; 8/405; 8/406; 8/416; 8/553; 8/554; 8/555; 8/647; 8/401; 435/184; 435/190; 435/191
(58) Field of Search .................. 8/410, 416, 553, 8/554, 555, 401, 405, 406, 647; 435/189, 190, 191

(56) References Cited

U.S. PATENT DOCUMENTS

| | | | |
|---|---|---|---|
| 3,251,742 A | 5/1966 | Soloway | 167/88 |
| 3,508,933 A | 4/1970 | Yates | 106/10 |
| 3,852,075 A | 12/1974 | Basadur | 106/11 |
| 3,907,799 A | 9/1975 | O'Brien et al. | 260/256 |
| 4,003,699 A | 1/1977 | Rose et al. | 8/10 |
| 4,157,388 A | 6/1979 | Christiansen | 424/70 |
| 4,217,914 A | 8/1980 | Jacquet et al. | 132/7 |
| 4,390,689 A | 6/1983 | Jacquet et al. | 528/335 |
| 4,702,906 A | 10/1987 | Jacquet et al. | 424/70 |
| 4,719,182 A | 1/1988 | Nadolsky et al. | 528/310 |
| 4,823,985 A | 4/1989 | Grollier et al. | 221/1 |
| 5,061,289 A | 10/1991 | Clausen et al. | 8/405 |
| 5,380,340 A | 1/1995 | Neunhoeffer et al. | 8/409 |
| 5,578,087 A * | 11/1996 | Audousset et al. | 8/409 |
| 5,735,908 A * | 4/1998 | Cotteret et al. | 8/410 |
| 5,766,576 A | 6/1998 | Löwe et al. | 424/62 |
| 6,132,707 A * | 10/2000 | Dubief et al. | 424/78.08 |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 189 935 | 8/1986 |
| EP | 0 504 005 | 9/1992 |
| EP | 557 203 | 8/1993 |
| EP | 0 628 559 | 12/1994 |
| EP | 0 673 641 | 9/1995 |
| FR | 2 112 549 | 6/1972 |
| FR | 2 270 846 | 12/1975 |
| FR | 2 586 913 | 3/1987 |
| FR | 2 694 018 | 1/1994 |
| FR | 2 733 749 | 11/1996 |
| GB | 1 026 978 | 4/1966 |
| GB | 1 153 196 | 5/1969 |
| GB | 1320250 | 6/1973 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 95/07988 | 3/1995 |
| WO | WO 95/33836 | 12/1995 |
| WO | WO 95/33837 | 12/1995 |
| WO | WO 96/00290 | 1/1996 |
| WO | WO 96/15765 | 5/1996 |
| WO | WO 97/19998 | 6/1997 |
| WO | WO-9719998 * | 6/1997 |
| WO | WO 97/19999 | 6/1997 |

OTHER PUBLICATIONS

Vishnu J. Ram et al., "Synthesis of bioisoseric pyrazolo [1–5–a]pyrimidines as leishmanicides", Indian Journal of Chemistry, vol. 34B, Jun. 1995, pp. 514–520.

Robert H. Springer et al., "Synthesis and Enzymic Activity of 6–Carbethoxy– and 6–Ethoxy–3,7–disubstituted–pyrazolo[1,5–a]pyrimidines and Related Derivatives as Adenosine Cyclic 3',5'–Phosphate Phosphodiesterase Inhibitors", J. Med. Chem., vol. 25, 1982, pp. 235–242.

Thomas Novinson et al., "Synthesis and Antifungal Properties of Certain 7–Alkylaminopyrazolo[1,5–a]pyrimidines", J. Med. Chem. vol. 20, No. 2, 1977, pp. 296–299.

Nadia S. Ibrahim et al., "Studies on 3,5–Diaminopyrazoles: Synthesis of New Polyfunctionally Substituted Pyrazoloazines and Pyrazoloazoles", Archiv der Pharmazie, vol. 320, No. 3, Mar. 1987, pp. 240–246.

Alexander McKillop et al., "Reaction of Hydrazine With β–Aminocrotononitrile: Synthesis of 2,7–Dimethyl–5–Aminopyrazolo[1,5–a]pyrimidine", Heterocycles, vol. 6, No. 9, 10, 1977, pp. 1355–1360.

Koji Saito et al., "The Reaction of Ethyl Ethoxymethylenecyanoacetate with Its Hydrazino Derivatives", Bulletin of the Chemical Society of Japan, vol. 47, No. 2, 1974, pp. 476–480.

Ermitas Alcalde, "Etude de la réaction du β–aminocrotonitrile et du α–formyl phénylacétonitrile avec l'hydrazine: synthèse d'amino–7 pyrazolo[1,5–a]pyrimidines", Journal of Heterocyclic Chemistry, vol. 11, No. 3, Jun. 1974, pp. 423–429.

Richard J. Crawford et al., "A Replacement for Rubine Dye for Detecting Cationics on Keratin", J. Soc. Cosmet. Chem., vol. 31, No. 5, Sep./Oct. 1980, pp. 273–278.

English language Derwent Abstract of EP 0 504 005. Sep. 1992.

English language Derwent Abstract of EP 0 557 203. Aug. 1993.

(List continued on next page.)

Primary Examiner—Yogendra N. Gupta
Assistant Examiner—Eisa Elhilo
(74) Attorney, Agent, or Firm—Finnegan, Henderson, Farabow, Garrett & Dunner, L.L.P.

(57) ABSTRACT

The invention concerns a ready-to-use composition for dyeing human keratinous fibers and more particularly human hair, comprising in support suitable for dyeing keratinous fibers: (a) at least an enzyme such as laccase; (b) at least a cationic substantive or particular amphoteric polymer; (c) at least an oxidation coloring agent, as well as the dyeing methods using said composition.

39 Claims, No Drawings

OTHER PUBLICATIONS

English language Derwent Abstract of FR 2 112 549. Apr. 1972.

English language Derwent Abstract of FR 2 694 018. Jan. 1994.

English language Derwent Abstract of FR 2 733 749. Nov. 1996.

English language Derwent Abstract of JP 2–19576. Jan. 1990.

English language Derwent Abstract of JP 5–163124. Jun. 1993.

* cited by examiner

DYEING COMPOSITION CONTAINING A LACCASE AND KERATINOUS FIBER DYEING METHODS USING SAME

The present invention relates to a dyeing composition for keratinous fibres comprising, in a carrier appropriate for dyeing keratinous fibres, at least one enzyme of the laccase type, at least one particular cationic or amphoteric substantive polymer and at least one oxidation dye, as well as its uses for dyeing keratinous fibres, in particular human hair.

It is known to dye keratinous fibres, and in particular human hair, with dyeing compositions containing oxidation dye precursors, in particular ortho- and para-phenylenediamines, ortho- or para-aminophenols, heterocyclic bases generally called oxidation bases. The oxidation dye precursors, or oxidation bases, are colourless or weakly coloured compounds which, combined with oxidizing products, can give rise to dye and coloured compounds by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of molecules used in oxidation bases and couplers allows a rich palette of colours to be obtained.

The so-called "permanent" colour obtained by means of these oxidation dyes should moreover satisfy a number of requirements. Thus, it should have no drawbacks from the toxicological point of view, it should make it possible to obtain shades of the desired intensity and it should exhibit good resistance towards external agents (light, adverse weather conditions, washing, permanent waving, perspiration, rubbing).

The dyes should also make it possible to cover grey hair, and thus should be the least selective possible, that is to say they should make it possible to obtain the smallest possible differences in colour all along the same keratinous fibre, which may indeed be differently sensitized (i.e. damaged) between its tip and its root.

The oxidation dyeing of keratinous fibres is generally carried out in an alkaline medium, in the presence of hydrogen peroxide. However, the use of alkaline media in the presence of hydrogen peroxide has the disadvantage of causing substantial degradation of the fibres, as well as decolouring of the keratinous fibres which is not always desirable.

The oxidation dyeing of keratinous fibres can also be carried out with the aid of oxidizing systems different from hydrogen peroxide such as enzymatic systems. Thus, it has already been proposed in U.S. Pat. No. 3,251,742, Patent Applications FR-A-2,112,549, FR-A-2,694,018, EP-A-0, 504,005, WO95/07988, WO95/33836, WO95/33837, WO96/00290, WO97/19998 and WO97/19999 to dye keratinous fibres with compositions comprising at least one oxidation dye in combination with enzymes of the laccase type, the said compositions being brought into contact with atmospheric oxygen. These dyeing formulations, although used under conditions which do not cause degradation of the keratinous fibres comparable to that caused by dyeings carried out in the presence of hydrogen peroxide, lead to colours which are still inadequate both from the point of view of homogeneity of the colour distributed along the fibre ("unison"), from the point of view of chromaticity (luminosity) and of the dyeing power.

The aim of the present invention is to solve the problems mentioned above.

The Applicant has surprisingly discovered novel dyeing compositions containing, as oxidizing system, at least one enzyme of the laccase type and at least one particular cationic or amphoteric substantive polymer which will be defined in greater detail below, capable of constituting, in the presence of oxidation dye(s) (oxidation bases and/or couplers), ready-to-use dyeing formulations giving colours which are more homogeneous, more intense and mote chromatic without causing significant degradation or decolouring of the keratinous fibres, which are not very selective and which are quite resistant to various attacks to which the hair may be subjected.

These discoveries form the basis of the present invention.

The first subject of the present invention is therefore a ready-to-use composition intended for the dyeing of keratinous fibres, in particular human keratinous fibres and more particularly human hair, comprising, in a carrier appropriate for dyeing, (a) at least one enzyme of the laccase type;
(b) at least one cationic or amphoteric substantive polymer chosen from the group consisting of:
 (i) Polyquaternium-24;
 (ii) copolymers of dimethyldiallylammonium halide;
 (iii) homopolymers and copolymers of methacryloyloxyethyltrimethylammonium halide;
 (iv) poly(quaternary ammonium) polymers chosen from those of formulae (I), (II) and (III) defined in the text which follows;
 (v) copolymers of vinylpyrrolidone containing cationic units;
 (vi) cationic polysiloxanes;
(c) at least one oxidation dye.

The laccase(s) used in the ready-to-use dye composition in accordance with the invention may be chosen in particular from laccases of plant origin, animal origin, fungal origin (yeasts, moulds, fungi) or bacterial origin, organisms which may be of mono- or pluricellular origin. They can be obtained by biotechnology.

Among the laccases of plant origin which can be used according to the invention, there may be mentioned the laccases produced by plants which perform chlorophyll synthesis as indicated in Application FR-A-2,694,018 such as those found in the extracts of Anacardiaceae such as for example the extracts of *Magnifera indica, Schinus molle* or *Pleiogynium timoriense,* in the extracts of Podocarpaceae, Rosmarinus off., *Solanum tuberosum,* Iris sp., Coffea sp., *Daucus carrota, Vinca minor, Persea americana, Catharenthus roseus,* Musa sp., *Malus pumila, Gingko biloba, Monotropa hypopithys* (Indian pipe), Aesculus sp., *Acer pseudoplatanus, Prunus persica, Pistacia palaestina.*

Among the laccases of fungal origin optionally obtained by biotechnology which can be used according to the invention, there may be mentioned the laccase(s) derived from *Polyporus versicolor, Rhizoctonia practicola* and *Rhus vernicifera* as indicated in Applications FR-A-2,112,549 and EP-A-504005, those described in Patent Application WO95/07988, WO95/33836, WO95/33837, WO96/00290, WO97/19998 and WO97/19999, whose content is an integral part of the present description, such as for example those derived from Scytalidium, *Polyporus pinsitus, Myceliophtora thermophila, Rhizoctonia solani, Pyricularia orizae,* or variants thereof. There may also be mentioned those derived from *Tramates versicolor, Fomes fomentarius, Chaetomium thermophile, Neurospora crassa, Coriolus versicol, Botrytis cinerea, Rigidoporus lignosus, Phellinus noxius, Pleurotus ostreatus, Aspergillus nidulans, Podospora anserina, Agari-* cus bisporus, Ganoderma lucidum, Glomerella cingulata, Lactarius piperatus, Russula delica, Heterobasidion annosum, Thelephora terrestris, Cladosporium cladosporiodes, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens and variants thereof.

The laccases of fungal origin optionally obtained by biotechnology will be preferably chosen.

The enzymatic activity of the laccases of the invention which have syringaldazine among their substrates can be defined from the oxidation of syringaldazine under aerobic conditions. The lacu unit corresponds to the quantity of enzyme catalysing the conversion of 1 mmol of syringaldazine per minute at pH 5.5 at 30° C. The unit u corresponds to the quantity of enzyme producing a delta absorbance at 530 nm of 0.001 per minute using syringaldazine as substrate, at 30° C. and at pH 6.5.

The enzymatic activity of the laccases of the invention can also be defined from the oxidation of para-phenylenediamine. The ulac unit corresponds to the quantity of enzyme producing a delta absorbance at 496.5 nm of 0.001 per minute using para-phenylenediamine as substrate (64 mM) at 30° C. and at pH 5. According to the invention, it is preferable to determine the enzymatic activity in ulac units.

The quantities of laccase used in the compositions of the invention will vary according to the nature of the laccase chosen. Preferably, they will vary from 0.5 to 2000 lacu, or from 1000 to $4 \times 10^7$ u units, or from 20 to $2 \times 10^6$ ulac units per 100 g of composition.

The substantive character (that is to say the capacity for deposition on the hair) of the polymers used in accordance with the invention is conventionally determined by means of the test described by Richard J. Crawford, Journal of the Society of Cosmetic Chemists, 1980, 31—(5)—pages 273 to 278 (development with Acid Red 80 dye).

These substantive polymers are in particular described in the literature in patent application EP-A-0,557,203.

"Polyquaternium-24" is a C.T.F.A. dictionary definition (5$^{th}$ edition, 1993) which designates a quaternary ammonium polymer of hydroxyethylcellulose which has reacted with an epoxide substituted with a lauryldimethylammonium group. This polymer is described in patent application EP-A-0,189,935 and is marketed under the name "Quatrisoft LM 200" by the company Union Carbide.

Among the substantive polymers of the copolymer of dimethyldiallylammonium halide type which can be used according to the invention, there may be mentioned in particular:
the copolymers of diallyldimethylammonium chloride and of acrylic acid such as that in the proportions (80/20 by weight) sold under the name Merquat 280 by the company Calgon;
the copolymers of dimethyldiallylammonium chloride and of acrylamide sold under the names Merquat 550 and Merquat S by the company Merck.

Among the substantive polymers of the polymer of methacryloyloxyethyltrimethylammonium halide type which can be used according to the invention, there may be mentioned in particular the products which are called in the CTFA dictionary (5$^{th}$ edition, 1993) "Polyquaternium 37", "Polyquaternium 32" and "Polyquaternium 35", which correspond respectively, in the case of "Polyquaternium 37", to crosslinked poly(methacryloyloxyethyltrimethylammonium chloride), as a 50% dispersion in mineral oil, sold under the name Salcare SC95 by the company Allied Colloids, in the case of "Polyquaternium 32", to the crosslinked copolymer of acrylamide and of methacryloyloxyethyltrimethylammonium chloride (20/80 by weight), as a 50% dispersion in mineral oil, sold under the name Salcare SC92 by the company Allied Colloids, and in the case of "Polyquaternium 35", to the methosulphate of the copolymer of methacryloyloxyethyltrimethylammonium and of methacryloyloxyethyldimethylacetylammonium, sold under the name Plex 7525L by the company Rohm GmbH.

The substantive polymers of the poly(quaternary ammonium) type which can be used according to the invention are the following:
the polymers prepared and described in French patent 2,270,846, consisting of recurring units corresponding to the following formula (I):

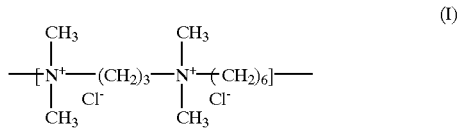

in particular those whose molecular weight, determined by gel permeation chromatography, is between 9500 and 9900;
the polymers prepared and described in French patent 2,270,846, consisting of recurring units corresponding to the following formula (II):

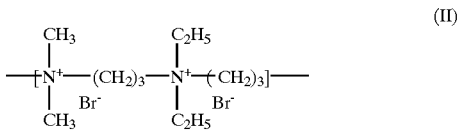

in particular those whose molecular weight, determined by gel permeation chromatography, is about 1200;
the polymers described and prepared in U.S. Pat. Nos. 4,157,388, 4,390,689, 4,702,906, 4,719,282, and consisting of recurring units corresponding to the following formula (III):

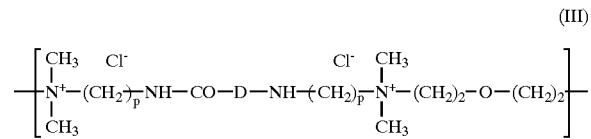

in which p denotes an integer varying from 1 to 6 approximately, D may be zero or may represent a group —$(CH_2)_r$—CO— in which r denotes a number equal to 4 or to 7,
and in particular those whose molecular mass is less than 100,000, preferably less than or equal to 50,000; such polymers are in particular sold by the company Miranol under the names "Mirapol A15", "Mirapol AD1, "Mirapol AZ1" and "Mirapol 175";

Among the polymers of vinylpyrrolidone (PVP) containing cationic units which can be used in accordance with the invention, there may be mentioned in particular:
a) the polymers of vinylpyrrolidone comprising dimethylaminoethyl methacrylate units; among these, there may be mentioned:
the vinylpyrrolidone/dimethylaminoethyl methacrylate (20/80 by weight) copolymer sold under the trade name COPOLYMER 845 by the company I.S.P.

the vinylpyrrolidone/dimethylaminoethyl methacrylate copolymers quaternized with diethyl sulphate, sold under the names GAFQUAT 734, 755, 755 S and 755 L by the company I.S.P.

the PVP/dimethylaminoethyl methacrylate/hydrophilic polyurethane copolymers sold under the trade name PECOGEL GC-310 by the company U.C.I.B. or alternatively under the names AQUAMERE C 1031 and C 1511 by the company BLAGDEN CHEMICALS, the guaternized or nonquaternized PVP/ dimethylaminoethyl methacrylate/C8 to C16 olefin copolymers sold under the names GANEX ACP 1050 to 1057, 1062 to 1069, 1079 to 1086, by the company I.S.P.

the PVP/dimethylaminoethyl methacrylate/ vinylcaprolactam copolymer sold under the name GAFFIX VC 713 by the company I.S.P.

b) the polymers of vinylpyrrolidone comprising methacrylamidopropyltrimethylammonium (M.A.P.T.A.C.) units, among which there may be mentioned:

the vinylpyrrolidone/(M.A.P.T.A.C.) copolymers sold under the trade names GAFQUAT ACP 1011 and GAFQUAT HS 100 by the company I.S.P.

c) the polymers of vinylpyrrolidone comprising methylvinylimidazolium units, among which there may be mentioned more particularly:

the PVP/methylvinylimidazolium chloride copolymers sold under the names LUVIQUAT FC 370, FC 550, FC 905, HM 552 by the company B.A.S.F.

the PVP/methylvinylimidazolium chloride/ vinylimidazole copolymer sold under the name LUVIQUAT 8155 by the company B.A.S.F.

the PVP/methylvinylimidazolium methosulphate copolymer sold under the name LUVIQUAT MS 370 by the company B.A.S.F.

Among the cationic polysiloxanes, there may be mentioned in particular those described in patent application EP-A-0,557,203, from page 8 line 48 to page 11 line 9, and still more particularly the products comprising Amodimethicone" (C.T.F.A. name) of the following formula (IV):

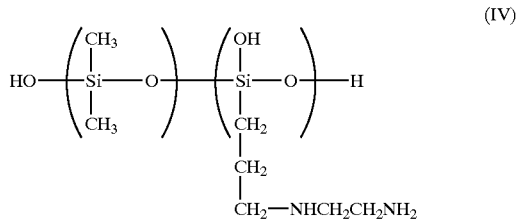

(IV)

The concentration of cationic or amphoteric substantive polymer may vary between 0.01 and 10% approximately relative to the total weight of the dyeing composition applied to the hair, and preferably between 0.1 and 5%.

The nature of the oxidation dye(s) (oxidation bases and/or couplers) used in the ready-to-use dyeing composition is not critical.

The oxidation bases may be chosen in particular from para-phenylenediamines, double bases, para-aminophenols, ortho-aminophenols and heterocyclic oxidation bases.

Among the para-phenylenediamines which can be used as oxidation base in the dyeing composition in accordance with the invention, there may be mentioned in particular the compounds of the following formula (V) and their addition salts with an acid:

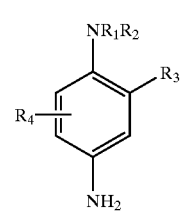

(V)

in which:

$R_1$ represents a hydrogen atom, a $C_1$–$C_4$ alkyl radical, a monohydroxy($C_1$–$C_4$ alkyl) radical, a polyhydroxy-($C_2$–$C_4$ alkyl) radical, a ($C_1$–$C_4$)alkoxy($C_1$–$C_4$)alkyl radical, a $C_1$–$C_4$ alkyl radical substituted with a nitrogen-containing group, a phenyl radical or a 4'-aminophenyl radical;

$R_2$ represents a hydrogen atom, a $C_1$–$C_4$ alkyl radical, a monohydroxy($C_1$–$C_4$ alkyl) radical, a polyhydroxy ($C_2$–$C_4$ alkyl) radical, a ($C_1$–$C_4$)alkoxy($C_1$–$C_4$)alkyl radical or a $C_1$–$C_4$ alkyl radical substituted with a nitrogen-containing group;

$R_3$ represents a hydrogen atom, a halogen atom such as a chlorine, bromine, iodine or fluorine atom, a $C_1$–$C_4$ alkyl radical, a monohydroxy($C_1$–$C_4$ alkyl) radical, a hydroxy($C_1$–$C_4$ alkoxy) radical, an acetylamino($C_1$–$C_4$ alkoxy) radical, a mesylamino($C_1$–$C_4$ alkoxy) radical or a carbamoylamino($C_1$–$C_4$ alkoxy) radical, $R_4$ represents a hydrogen or halogen atom or a $C_1$–$C_4$ alkyl radical.

Among the nitrogen-containing groups of formula (V) above, there may be mentioned in particular the amino, mono($C_1$–$C_4$)alkylamino, ($C_1$–$C_4$)dialkylamino, ($C_1$–$C_4$) trialkylamino, monohydroxy($C_1$–$C_4$)alkylamino, imidazolinium and ammonium radicals.

Among the para-phenylenediamines of formula (V) above, there may be mentioned more particularly para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and their addition salts with an acid.

Among the para-phenylenediamines of formula (V) above, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-paraphenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid.

According to the invention, "double bases" is understood to mean the compounds containing at least two aromatic rings on which amino and/or hydroxyl groups are carried.

Among the double bases which can be used as oxidation bases in the dyeing compositions in accordance with the invention, there may be mentioned in particular the compounds corresponding to the following formula (VI), and their addition salts with an acid:

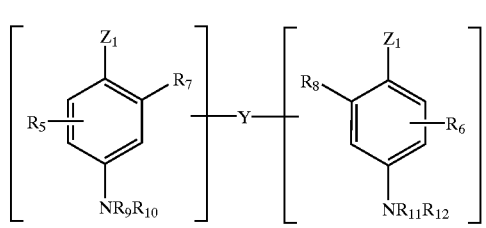

(VI)

in which:

$Z_1$ and $Z_2$, which are identical or different, represent a hydroxyl or —$NH_2$ radical which may be substituted with a $C_1$–$C_4$ alkyl radical or with a linking arm Y;

the linking arm Y represents a linear or branched alkylene chain comprising from 1 to 14 carbon atoms, which may be interrupted by or which may end with one or more nitrogen-containing groups and/or one or more heteroatoms such as oxygen, sulphur or nitrogen atoms, and optionally substituted with one or more hydroxyl or $C_1$–$C_6$ alkoxy radicals;

$R_5$ and $R_6$ represent a hydrogen or halogen atom, a $C_1$–$C_4$ alkyl radical, a monohydroxy($C_1$–$C_4$ alkyl) radical, a polyhydroxy($C_2$–$C_4$ alkyl) radical, an amino($C_1$–$C_4$ alkyl) radical or a linking arm Y;

$R_7$, $R_8$, $R_9$, $R_{10}$, $R_{11}$ and $R_{12}$, which are identical or different, represent a hydrogen atom, a linking arm Y or a $C_1$–$C_4$ alkyl radical; it being understood that the compounds of formula (VI) contain only one linking arm Y per molecule.

Among the nitrogen-containing groups of formula (VI) above, there may be mentioned in particular the amino, mono($C_1$–$C_4$)alkylamino, ($C_1$–$C_4$)dialkylamino, ($C_1$–$C_4$) trialkylamino, monohydroxy($C_1$–$C_4$)alkylamino, imidazolinium and ammonium radicals.

Among the double bases of formulae (VI) above, there may be mentioned more particularly N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and their addition salts with an acid.

Among these double bases of formula (VI), N,N'-bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid are particularly preferred.

Among the para-aminophenols which can be used as oxidation bases in the dyeing compositions in accordance with the invention, there may be mentioned in particular the compounds corresponding to the following formula (VII), and their addition salts with an acid:

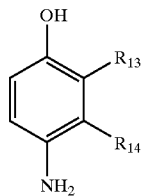

(VII)

in which:

$R_{13}$ represents a hydrogen or halogen atom, a $C_1$–$C_4$ alkyl, monohydroxy($C_1$–$C_4$ alkyl), ($C_1$–$C_4$)alkoxy ($C_1$–$C_4$)alkyl, amino($C_1$–$C_4$ alkyl) or hydroxy($C_1$–$C_4$) alkylamino($C_1$–$C_4$ alkyl) radical, $R_{14}$ represents a hydrogen or halogen atom, a $C_1$–$C_4$ alkyl, monohydroxy($C_1$–$C_4$ alkyl), polyhydroxy ($C_2$–$C_4$ alkyl), amino($C_1$–$C_4$ alkyl), cyano($C_1$–$C_4$ alkyl) or ($C_1$–$C_4$)alkoxy($C_1$–$C_4$)alkyl radical, it being understood that at least one of the radicals $R_{13}$ or $R_{14}$ represents a hydrogen atom.

Among the para-aminophenols of formula (VII) above, there may be mentioned more particularly para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid.

Among the ortho-aminophenols which can be used as oxidation bases in the dyeing compositions in accordance with the invention, there may be mentioned more particularly 2-aminophenol, 2-amino-5-methylphenol, 2-amino-6-methylphenol, 5-acetamido-2-aminophenol, and their addition salts with an acid.

Among the heterocyclic bases which can be used as oxidation bases in the dyeing compositions in accordance with the invention, there may be mentioned more particularly pyridine derivatives, pyrimidine derivatives, pyrazole derivatives, pyrazolopyrimidine derivatives, and their addition salts with an acid.

Among the pyridine derivatives, there may be mentioned more particularly the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Among the pyrimidine derivatives, there may be mentioned more particularly the compounds described for example in German Patent DE 2,359,399 or Japanese Patents JP 88-169,571 and JP 91-333,495 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and their addition salts with an acid.

Among the pyrazole derivatives, there may be mentioned more particularly the compounds described in Patents DE 3,843,892, DE 4,133,957 and Patent Applications WO 94/08969, WO 94/08970, FR-A-2,733,749 and DE 195 43 988 such as 4,5-diamino-1-methylpyrazole, 3,4-diaminopyrazole, 4,5-diamino-1-(4'-chlorobenzyl)-pyrazole, 4,5-diamino-1,3-dimethylpyrazole, 4,5-diamino- 3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts with an acid.

Among the pyrazolopyrimidine derivatives, there may be mentioned more particularly the pyrazolo[1,5-a]pyrimidines of the following formula (VIII), their addition salts with an acid or with a base and their tautomeric forms, when a tautomeric equilibrium exists:

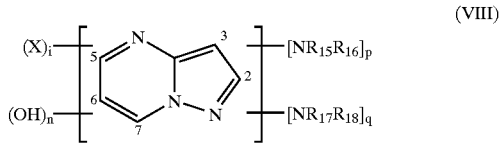

in which:

R$_{15}$, R$_{16}$, R$_{17}$ and R$_{18}$, which are identical or different, denote a hydrogen atom, a C$_1$–C$_4$ alkyl radical, an aryl radical, a C$_1$–C$_4$ hydroxyalkyl radical, a C$_2$–C$_4$ polyhydroxyalkyl radical, a (C$_1$–C$_4$)alkoxy(C$_1$–C$_4$ alkyl) radical, a C$_1$–C$_4$ aminoalkyl radical (it being possible for the amine to be protected with an acetyl, ureido or sulphonyl radical), a (C$_1$–C$_4$)alkylamino(C$_1$–C$_4$ alkyl) radical, a di-[(C$_1$–C$_4$)alkyl]amino(C$_1$–C$_4$ alkyl) radical (it being possible for the dialkyl radicals to form a carbon-containing ring or a 5- or 6-membered heterocycle), a hydroxy(C$_1$–C$_4$)alkyl- or di-[hydroxy(C$_{1-4}$)alkyl]-amino(C$_1$–C$_4$ alkyl) radical, the X radicals, which are identical or different, denote a hydrogen atom, a C$_1$–C$_4$ alkyl radical, an aryl radical, a C$_1$–C$_4$ hydroxyalkyl radical, a C$_2$–C$_4$ polyhydroxyalkyl radical, a C$_1$–C$_4$ aminoalkyl radical, a (C$_1$–C$_4$) alkylamino(C$_1$–C$_4$ alkyl) radical, a di-[(C$_1$–C$_4$)alkyl] amino(C$_1$–C$_4$ alkyl) radical (it being possible for the dialkyls to form a carbon-containing ring or a 5- or 6-membered heterocycle), a hydroxy(C$_1$–C$_4$)alkyl or di-[hydroxy(C$_1$–C$_4$)alkyl]-amino(C$_1$–C$_4$ alkyl) radical, an amino radical, a (C$_1$–C$_4$)alkyl- or di-[(C$_1$–C$_4$)alkyl]-amino radical; a halogen atom, a carboxylic acid group, a sulphonic acid group;

i equals 0, 1, 2 or 3;
p equals 0 or 1;
q equals 0 or 1;
n equals 0 or 1;
with the proviso that:
the sum p+q is different from 0;
when p+q is equal to 2, then n equals 0 and the groups NR$_{15}$R$_{16}$ and NR$_{17}$R$_{18}$ occupy positions (2,3); (5,6); (6,7); (3,5) or (3,7);
when p+q is equal to 1, then n equals 1 and the group NR$_{15}$R$_{16}$ (or NR$_{17}$R$_{18}$) and the OH group occupy positions (2,3); (5,6); (6,7); (3,5) or (3,7).

When the pyrazolo[1,5-a]pyrimidines of formula (VIII) above are such that they comprise a hydroxyl group on one of the positions 2, 5 or 7 at the α position with respect to a nitrogen atom, a tautomeric equilibrium exists which is represented for example by the following scheme:

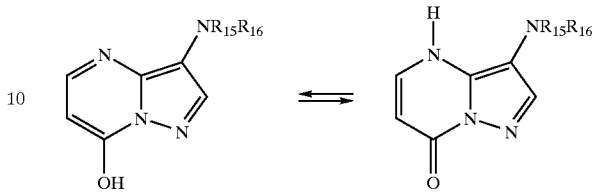

Among the pyrazolo[1,5-a]pyrimidines of formula (VIII) above, there may be mentioned in particular:

pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)(2-hydroxyethyl)amino]ethanol;
2-[(7-aminopyrazolo[1,5-a]pyrimidin-3-yl)(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;

and their addition salts and their tautomeric forms, when a tautomeric equilibrium exists.

The pyrazolo[1,5-a]pyrimidines of formula (VIII) above may be prepared by cyclization from an aminopyrazole according to the syntheses described in the following references:
EP 628559 BEIERSDORF-LILLY
R. Vishdu, H. Navedul, Indian J. Chem., 34b(6), 514, 1995.
N. S. Ibrahim, K. U. Sadek, F. A. Abdel-Al, Arch. Pharm., 320, 240, 1987.
R. H. Springer, M. B. Scholten, D. E. O'Brien, T. Novinson, J. P. Miller, R. K. Robins, J. Med. Chem., 25, 235, 1982.
T. Novinson, R. K. Robins, T. R. Matthews, J. Med. Chem., 20, 296, 1977.
U.S. Pat. No. 3,907,799 ICN PHARMACEUTICALS The pyrazolo[1,5-a]pyrimidines of formula (VIII) above can also be prepared by cyclization from hydrazine according to the syntheses described in the following references:
A. McKillop and R. J. Kobilecki, Heterocycles, 6(9), 1355, 1977.
E. Alcade, J. De Mendoza, J. M. Marcia-Marquina, C. Almera, J. Elguero, J. Heterocyclic Chem., 11(3), 423, 1974.
K. Saito, I. Hori, M. Higarashi, H. Midorikawa, Bull. Chem. Soc. Japan, 47(2), 476, 1974.

The oxidation base(s) in accordance with the invention preferably represent from 0.0005 to 12% by weight approximately of the total weight of the ready-to-use dyeing composition, and still more preferably from 0.005 to 6% by weight approximately of this weight.

The couplers which can be used are those conventionally used in oxidation dyeing compositions, that is to say meta-phenylenediamines, meta-aminophenols and meta-diphenols, mono- or polyhydroxylated naphthalene derivatives, sesamol and its derivatives and heterocyclic compounds such as, for example, indole derivatives, indoline derivatives, benzimidazole derivatives, benzomorpholine derivatives, sesamol derivatives, pyrazoloazole derivatives, pyrroloazole derivatives, imidazoloazole derivatives, pyrazolopyrimidine derivatives 3,5-pyrazolinedione derivatives, pyrrolo[3,2-d]oxazole derivatives, pyrazolo[3,4-d]thiazole derivatives, thiazoloazole S-oxide derivatives, thiazoloazole S,S-dioxide derivatives, and their addition salts with an acid.

These couplers may be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo[1,5-a]benzimidazole, and their addition salts with an acid.

These couplers preferably represent from 0.0001 to 10% by weight approximately of the total weight of the ready-to-use dyeing composition, and still more preferably from 0.005 to 5% by weight approximately of this weight.

In general, the addition salts with an acid which can be used in the context of the dyeing compositions of the invention (oxidation bases and couplers) are in particular chosen from hydrochlorides, hydrobromides, sulphates and tartrates, lactates and acetates.

The dyeing composition of the invention may also contain, in addition to the oxidation dyes defined above, direct dyes in order to increase the shimmer of the shades. These direct dyes may then in particular be chosen from nitro, azo and anthraquinone dyes.

The subject of the invention is also a method of dyeing keratinous fibres, and in particular human keratinous fibres such as hair, using the ready-to-use dyeing composition as defined above.

According to this method, at least one ready-to-use dyeing composition as defined above is applied to the fibres for a sufficient time to develop the desired colour, after which they are rinsed, optionally washed with shampoo, rinsed again and dried.

The time necessary for the development of the colour on the keratinous fibres is generally between 3 and 60 minutes and still more precisely 5 and 40 minutes.

According to one particular embodiment of the invention, the method comprises a preliminary step consisting in storing in a separate form, on the one hand, a composition (A) comprising, in a medium appropriate for dyeing, at least one oxidation dye as defined above and, on the other hand, a composition (B) containing, in a medium appropriate for dyeing, at least one enzyme of the laccase type and at least at least one cationic or amphoteric substantive polymer, and then in mixing them at the time of use before applying this mixture to the keratinous fibres.

According to one specific embodiment of the invention, the cationic or amphoteric substantive polymer may be incorporated into the composition (A).

Another subject of the invention is a multi-compartment device or dyeing "kit" or any other multi-compartment packaging system in which a first comparment contains the composition (A) as defined above and a second compartment contains a composition (B) as defined above. These devices may be equipped with a means which makes it possible to deliver the desired mixture to the hair, such as the devices described in Patent FR-2,586,913 in the name of the applicant.

The medium appropriate for keratinous fibres (or carrier) of the ready-to-use dyeing compositions in accordance with the invention generally consists of water or of a mixture of water and of at least one organic solvent in order to solubilize the compounds which might not be sufficiently soluble in water. As organic solvent, there may be mentioned for example $C_1$–$C_4$ alkanols such as ethanol and isopropanol as well as aromatic alcohols such as benzyl alcohol, similar products and mixtures thereof.

The solvents may be present in proportions preferably of between 1 and 40% by weight approximately relative to the total weight of the dyeing composition, and still more preferably between 5 and 30% by weight approximately.

The pH of the ready-to-use dyeing compositions in accordance with the invention is chosen such that the enzymatic activity of the laccase is not impaired. It varies generally from 4 to 11 approximately, and more preferably from 6 to 9 approximately.

The ready-to-use dyeing compositions in accordance with the invention may also contain various adjuvants conventionally used in dyeing compositions, such as anionic, cationic, nonionic, amphoteric or zwitterionic surfactants or mixtures thereof, polymers, thickeners, antioxidants, enzymes different from the laccases used in accordance with the invention, such as for example peroxidases or oxidoreductases containing 2 electrons, penetrating agents, sequestering agents, perfumes, buffers, dispersing agents, film-forming agents, screening agents, vitamins, preservatives or opacifying agents.

Of course, persons skilled in the art will be careful to choose this or these optional additional compounds such that the advantageous properties intrinsically attached to the compositions in accordance with the invention are not, or substantially not, impaired by the addition(s) envisaged.

The ready-to-use dyeing compositions in accordance with the invention can be provided in various forms, such as in the form of liquids, creams, gels, optionally pressurized, or in any other form appropriate for dyeing keratinous fibres, in particular human hair.

In the case of a ready-to-use dyeing composition, the oxidation dye(s) and the laccase(s) are present in the said composition which should be free of gaseous oxygen, so as to avoid any premature oxidation of the oxidation dye(s).

Concrete examples illustrating the invention will now be given.

In the text which follows or in the preceding text, unless otherwise stated, the percentages are expressed by weight.

The following examples illustrate the invention with no limitation being implied.

DYEING EXAMPLES 1 TO 3

The following ready-to-use dyeing compositions were prepared (contents in grams):

| COMPOSITION | 1 | 2 | 3 |
| --- | --- | --- | --- |
| Laccase derived from Rhus vernicifera containing 180 units/mg sold by the company SIGMA | 1.8 | 1.8 | 1.8 |
| para-Phenylenediamine | 0.254 | 0.254 | 0.254 |
| 2,4-diaminophenoxyethanol.2HCl | 0.260 | 0.260 | 0.260 |
| Ethanol | 20 | 20 | 20 |

-continued

| COMPOSITION | 1 | 2 | 3 |
|---|---|---|---|
| Alkylpolyglucoside in aqueous solution containing 60% of active substance (AS) sold under the name ORAMIX CG110 by the company SEPPIC | 4.800 | 4.800 | 4.800 |
| Substantive polymer | 1 (AS) | 1 (AS) | 1 (AS) |
| pH agent qs pH | 6.5 | 6.5 | 6.5 |
| Demineralized water qs | 100 | 100 | 100 |

Substantive polymer of composition (1):
  polydimethylsiloxane containing aminomethylaminoisobutyl groups/polydimethylsiloxane mixture sold under the name Q2 8220 by the company DOW CORNING.
Substantive polymer of composition (2):
  dimethyldiallylammonium chloride/acrylic acid copolymer as 40.5% aqueous solution, sold under the name MERQUAT 280 by the company CALGON.
Substantive polymer of composition (3):
  polymer of formula (I) [tetramethylhexamethylenediamine/1,3-dichloropropylenediamine polycondensate as a 60% aqueous solution].

The ready-to-use dyeing compositions described above were applied at the temperature of 30° C. to locks of natural grey hair which is 90% white for 40 minutes. The hair was then rinsed, washed with a standard shampoo and then dried. The hair was dyed bluish grey in the three cases.

In the examples described above, 1.8% of *Rhus vernicifera* laccase at 180 units/mg can be replaced by 1% of Pyricularia Orizae laccase at 100 units/mg sold by the company I.C.N.

What is claimed is:

1. A composition for dyeing keratinous fibers comprising:

(a) at least one enzyme of the laccase type;
  (b) at least one cationic substantive polymer, at least one amphoteric substantive polymer or at least one mixture thereof, wherein said substantive polymers are chosen from:
    (i) Polyquaternium-24;
    (ii) copolymers derived from monomers of dimethyldiallylammonium halide;
    (iii) homopolymers and copolymers derived from monomers of methacryloyloxyethyltrimethylammonium halide;
    (iv) poly(quaternary ammonium) polymers chosen from formulae (I), (II) and (III):
      polymers comprising units of formula (I):

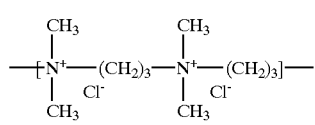

polymers comprising units of formula (II):

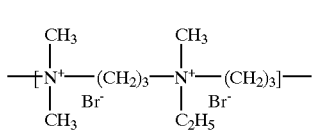

polymers comprising units of formula (III):

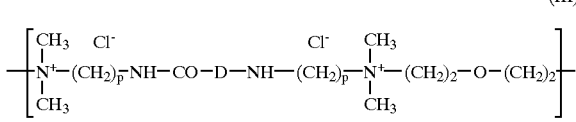

in which p is an integer ranging from 1 to 6, D is chosen from a bond, and
      —(CH$_2$)$_r$—CO— groups, in which r is chosen from 4 and 7;
    (v) polymers derived from monomers of vinylpyrrolidone comprising cationic units; and
    (vi) cationic polysiloxanes chosen from products derived from amodimethicones of formula (IV):

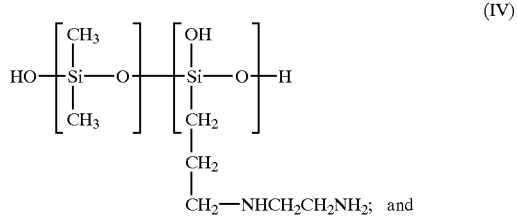

(c) at least one oxidation dye and the acid addition salts thereof; with the proviso that the composition does not comprise hydrogen peroxide.

2. A composition according to claim 1, wherein said keratinous fibers are human keratinous fibers.

3. A composition according to claim 2, wherein said human keratinous fibers are hair.

4. A composition according to claim 1, wherein said at least one enzyme of the laccase type is chosen from laccases of plant origin, animal origin, fungal origin, bacterial origin and laccases obtained by biotechnology.

5. A composition according to claim 1, wherein said at least one enzyme of the laccase type is chosen from those produced by plants performing chlorophyll synthesis.

6. A composition according to claim 1, wherein said at least one enzyme of the laccase type is chosen from those extracted from plants chosen from Anacardiaceae, Podocarpaceae, Rosmarinus off., *Solanum tuberosum*, Iris sp., *Coffea* sp., *Daucus Carrota*, *Vinca minor*, *Persea americana*, *Catharenthus roseus*, *Musa* sp., *Malus pumila*, *Gingko biloba*, *Monotropa hypopithys*, *Aesculus* sp., *Acer pseudoplatanus*, *Prunus persica* and *Pistacia palaestina*.

7. A composition according to claim 1, wherein said at least one enzyme of the laccase type is chosen from those derived from fungi chosen from *Pyricularia orizae*, *Polyporus versicolor*, *Rhizoctonia praticola*, *Rhus vernicifera*, Scytalidium, *Polyporus pinsitus*, *Myceliophtora thermophila*, *Rhizoctonia solani*, *Tramates versicolor*, *Fomes fomentarius*, *Chaetomium thermophile*, *Neurospora crassa*, *Coriolus versicol*, *Botrytis cinerea*, *Rigidoporus lignosus*, *Phellinus noxius*, *Pleurotus ostreatus*, *Aspergillus*

*nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens* and variants of all of said fungi.

8. A composition according to claim 1, wherein said at least one enzyme of the laccase type is present in a quantity ranging from 0.5 to 2000 lacu units per 100 g of said composition.

9. A composition according to claim 1, wherein said at least one enzyme of the laccase type is present in a quantity ranging from 1000 to $4 \times 10^7$ u units per 100 g of said composition.

10. A composition according to claim 1, wherein said at least one enzyme of the laccase type is present in a quantity ranging from 20 to $2 \times 10^6$ ulac units per 100 g of said composition.

11. A composition according to claim 1, wherein said copolymers derived from monomers of dimethyldiallylammonium halide are chosen from:
    copolymers derived from monomers of (i) diallyldimethylammonium chloride and (ii) acrylic acid; and
    copolymers derived from monomers of (i) diallyldimethylammonium chloride and (ii) acrylamide.

12. A composition according to claim 1, wherein said homopolymers and copolymers derived from monomers of methacryloyloxyethyltrimethylammonium halide are chosen from:
    crosslinked poly(methacryloyloxyethyltrimethylammonium chloride) homopolymers present as a 50% dispersion in mineral oil;
    crosslinked copolymers derived from monomers of (i) acrylamide and (ii) methacryloyloxyethyltrimethylammonium chloride (20/80 by weight) present as a 50% dispersion in mineral oil; and
    methosulphates of copolymers derived from monomers of
    (i) methacryloyloxyethyltrimethylammonium and
    (ii) methacryloyloxyethyldimethylacetylammonium.

13. A composition according to claim 1, wherein said polymers derived from monomers of vinylpyrrolidone comprising cationic units are chosen from:
    polymers of vinylpyrrolidone comprising units derived from dimethylaminoethyl methacrylate;
    polymers of vinylpyrrolidone comprising units derived from methacrylamidopropyltrimethylammonium; and
    polymers of vinylpyrrolidone comprising units derived from methylvinylimidazolium.

14. A composition according to claim 1, wherein said at least one substantive polymer is present in a concentration ranging from approximately 0.01 to approximately 10% by weight relative to the total weight of said composition.

15. A composition according to claim 1, wherein said at least one substantive polymer is present in a concentration ranging from approximately 0.1% to approximately 5% by weight relative to the total weight of said composition.

16. A composition according to claim 1, wherein said at least one oxidation dye is chosen from oxidation bases, couplers and the acid addition salts of all said at least one oxidation dyes.

17. A composition according to claim 16, wherein said oxidation bases are chosen from para-phenylenediamines, double bases, ortho-aminophenols, para-aminophenols, heterocyclic bases and the acid addition salts of all of said oxidation bases.

18. A composition according to claim 16, wherein said couplers are chosen from meta-phenylenediamines, meta-aminophenols, meta-diphenols, heterocyclic couplers and the acid addition salts of all of said couplers.

19. A composition according to claim 16, wherein said at least one oxidation dye is chosen from oxidation bases present in a concentration ranging from 0.0005% to 12% by weight relative to the total weight of said composition.

20. A composition according to claim 19, wherein said at least one oxidation dye is chosen from oxidation bases present in a concentration ranging from 0.005% to 6% by weight relative to the total weight of said composition.

21. A composition according to claim 20, wherein said at least one oxidation dye is chosen from couplers present in a concentration ranging from 0.0001% to 10% by weight relative to the total weight of said composition.

22. A composition according to claim 16, wherein said at least one oxidation dye is chosen from couplers present in a concentration ranging from 0.005% to 5% by weight relative to the total weight of said composition.

23. A composition according to claim 16, wherein said acid addition salts are chosen from hydrochlorides, hydrobromides, sulphates, tartrates, lactates and acetates.

24. A composition according to claim 16, wherein said couplers are chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxy-benzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy) propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyraxol-5-one, 2,6-dimethyl-pyrazolo[1,5-b]-1,2,4-triazole, 2,6-dimethyl[3,2-c]-1,2,4-triazole, 6-methylpyrazolo[1,5-a]-benzimidazole and the acid addition salts of all of said couplers.

25. A composition according to claim 1, further comprising at least one direct dye.

26. A composition according to claim 25, wherein said at least one direct dye is chosen from nitro, azo and anthraquinone dyes.

27. A composition according to claim 1, further comprising at least one carrier appropriate for keratinous fibers.

28. A composition according to claim 27, wherein said at least one carrier is chosen from water and organic solvents.

29. A composition according to claim 28, wherein said at least one carrier is chosen from organic solvents present in a concentration ranging from approximately 1% to approximately 40% by weight relative to the total weight of said composition.

30. A composition according to claim 29, wherein said at least one carrier is chosen from organic solvents present in a concentration ranging from approximately 5% to approximately 30% by weight relative to the total weight of said composition.

31. A composition according to claim 1, wherein the pH varies from approximately 4 to approximately 11.

32. A composition according to claim 31, wherein said pH varies from approximately 6 to approximately 9.

33. A composition according to claim 1, further comprising at least one suitable cosmetic adjuvant chosen from surfactants, polymers differing from said polymers as defined in claim 1 thickeners, antioxidants, enzymes different from said at least one enzyme of the laccase type as defined in claim 1, penetrating agents, sequestering agents, perfumes, buffers, dispersing agents, film-forming agents, screening agents, vitamins, preservatives and opacifying agents.

34. A composition according to claim 1, wherein said composition is a ready-to-use composition.

35. A method of dyeing keratinous fibers comprising applying to said keratinous fibers for a sufficient time to develop a desired color at least one dyeing composition comprising:
    (a) at least one enzyme of the laccase type;
    (b) at least one cationic substantive polymer, at least one amphoteric substantive polymer or at least one mixture thereof, wherein said substantive polymers are chosen from:
        (i) Polyquaternium-24;
        (ii) copolymers derived from monomers of dimethyldiallylammonium halide;
        (iii) homopolymers and copolymers derived from monomers of methacryloyloxyethyltrimethylammonium halide;
        (iv) poly(quaternary ammonium) polymers chosen from formulae (I), (II) and (III):
            polymers comprising recurring units of formula (I):

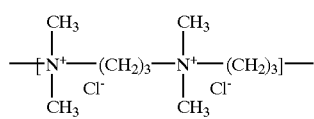

(I)

polymers comprising recurring units of formula (II):

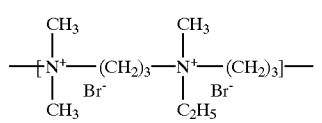

(II)

polymers comprising recurring units of formula (III):

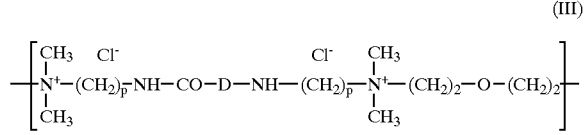

(III)

in which p is an integer ranging from 1 to 6, D is chosen from a bond and
            —(CH$_2$)$_r$—CO— groups, in which r is chosen from 4 and 7;
        (v) polymers derived from monomers of vinylpyrrolidone comprising cationic units; and
        (vi) cationic polysiloxanes chosen from products derived from amodimethicone of formula (IV):

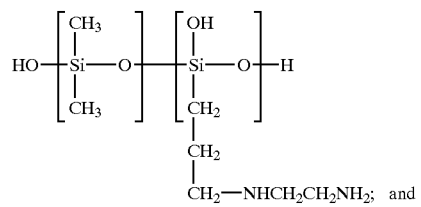

(IV)

(c) at least one oxidation dye and the acid addition salts thereof;

with the proviso that the dyeing composition does not comprise hydrogen peroxide.

36. A method of dyeing keratinous fibers according to claim 35, wherein said keratinous fibers are human keratinous fibers.

37. A method of dyeing keratinous fiber according to claim 36, wherein said human keratinous fibers are hair.

38. A method for dyeing keratinous fibres comprising:
    (a) storing a first composition,
    (b) storing a second composition separately from said first composition,
    (c) mixing the first composition with the second composition to form a mixture, and
    (d) applying said mixture to said keratinous fibres for a time sufficient to achieve a desired colouration,
        wherein said first composition comprises at least one oxidation dye and optionally comprises at least one substantive polymer, in a medium suitable for keratinous fibres, and
        wherein said second composition comprises at least one enzyme of the laccase type and optionally comprises at least one substantive polymer in a medium suitable for keratinous fibres, one of said first and second compositions comprising said at least one substantive polymer;
        with the proviso that neither the first nor second composition comprises hydrogen peroxide.

39. A multicompartment device or a dyeing kit comprising a first compartment containing a composition (A) comprising, in a medium appropriate for dyeing, at least one oxidation dye, and a second compartment containing a composition (B) comprising, in a medium appropriate for keratinous fibers, at least one enzyme of the laccase type, wherein said at least one of said composition (A) and said composition (B) comprises said at least one substantive polymer;
        with the proviso that neither composition (A) nor composition (B) comprises hydrogen peroxide.

* * * * *

UNITED STATES PATENT AND TRADEMARK OFFICE
CERTIFICATE OF CORRECTION

PATENT NO.    : 6,471,730 B1                                      Page 1 of 1
DATED         : October 29, 2002
INVENTOR(S)   : Gérard Lang and Jean Cotteret It is certified that error appears in the above-identified patent and that said Letters Patent is hereby corrected as shown below:

Title page,
"[22] Filed: Sep. 11, 2000" should read:
-- [22]  PCT Filed: Dec. 18, 1998
   [86]  PCT No.: PCT/FR98/02794
         § 371 date: Sep. 11, 2000
         § 102(e) date: Sep. 11, 2000
   [87]  PCT Publ. No.: WO 99/36035
         PCT Publ. Date: Jul. 22, 1999 --.

Column 16,
Line 37, "methylpyraxol" should read -- methylpyrazol --.
Line 67, after "claim 1" insert a comma.

Signed and Sealed this

Fifteenth Day of April, 2003

JAMES E. ROGAN
*Director of the United States Patent and Trademark Office*